(12) United States Patent
Godshall et al.

(10) Patent No.: US 10,413,647 B2
(45) Date of Patent: Sep. 17, 2019

(54) IMPLANTABLE MECHANICAL CIRCULATORY SUPPORT DEVICES

(71) Applicant: HeartWare, Inc., MoundsView, MN (US)

(72) Inventors: Douglas Godshall, Medfield, MA (US); Mustafa Ertan Taskin, Cooper City, FL (US); Jeffrey A. Larose, Sunrise, FL (US); Nick Youker, River Falls, WI (US); Andre Simon, Harefield (GB)

(73) Assignee: HeartWare, Inc., Miami Lakes, FL (US)

( * ) Notice: Subject to any disclaimer, the term of this patent is extended or adjusted under 35 U.S.C. 154(b) by 209 days.

(21) Appl. No.: 15/385,456

(22) Filed: Dec. 20, 2016

(65) Prior Publication Data

US 2017/0173238 A1      Jun. 22, 2017

Related U.S. Application Data

(60) Provisional application No. 62/270,156, filed on Dec. 21, 2015.

(51) Int. Cl.
*A61M 1/00* (2006.01)
*A61M 1/10* (2006.01)
*A61M 1/12* (2006.01)

(52) U.S. Cl.
CPC .......... *A61M 1/1036* (2014.02); *A61M 1/101* (2013.01); *A61M 1/1086* (2013.01); *A61M 1/122* (2014.02); *A61M 2205/18* (2013.01); *A61M 2205/3334* (2013.01); *A61M 2205/3365* (2013.01); *A61M 2205/8206* (2013.01)

(58) Field of Classification Search
USPC .......................................................... 600/16
See application file for complete search history.

(56) References Cited

U.S. PATENT DOCUMENTS

| 4,838,889 A | 6/1989 | Kolff |
| 6,530,876 B1 | 3/2003 | Spence |
| 6,723,039 B2 | 4/2004 | French et al. |

(Continued)

FOREIGN PATENT DOCUMENTS

WO    2011081626 A1    7/2011

OTHER PUBLICATIONS

International Search Report and Written Opinion dated Mar. 7, 2017, for corresponding International Application No. PCT/US2016/067836; International Filing Date: Dec. 20, 2016 consisting of 10 pages.

(Continued)

*Primary Examiner* — Nicole F Lavert
(74) *Attorney, Agent, or Firm* — Christopher & Weisberg, P.A.

(57) ABSTRACT

A mechanical circulatory support device. The mechanical circulatory support device includes an inner casing defining a fluid flow path, the fluid flow path defines a longitudinal axis. A rotor is mounted within the fluid flow path and configured to rotate about the longitudinal axis. A housing is included, the inner casing and the rotor being substantially disposed within the housing. The housing having a cross-sectional shape in a plane transverse to the longitudinal axis which decreases in thickness extending from a medial position to opposite lateral positions.

13 Claims, 11 Drawing Sheets

(56) References Cited

U.S. PATENT DOCUMENTS

| | | |
|---|---|---|
| 7,684,864 B2 | 3/2010 | Olson et al. |
| 7,766,813 B2 | 8/2010 | Spence |
| 7,905,823 B2 | 3/2011 | Farnan et al. |
| 7,972,122 B2 | 7/2011 | LaRose et al. |
| 8,007,254 B2 | 8/2011 | LaRose et al. |
| 8,376,927 B2 | 2/2013 | Lopez |
| 8,419,609 B2 | 4/2013 | Shambaugh, Jr. et al. |
| 8,597,350 B2 | 12/2013 | Rudser et al. |
| 8,628,460 B2 | 1/2014 | Yomtov et al. |
| 8,768,487 B2 | 7/2014 | Farnan et al. |
| 2002/0161274 A1 | 10/2002 | French et al. |
| 2005/0135948 A1* | 6/2005 | Olsen .................. F16C 32/0448 417/423.12 |
| 2011/0238172 A1 | 9/2011 | Akdis |
| 2014/0273602 A1 | 9/2014 | Bondhus et al. |
| 2014/0275723 A1 | 9/2014 | Fritz, IV et al. |
| 2014/0336446 A1* | 11/2014 | Rodefeld .............. A61M 1/101 600/16 |
| 2015/0051438 A1 | 2/2015 | Taskin |

OTHER PUBLICATIONS

Klotz, S. et al., Partial Mechanical Long-Term Support with the CircuLite Synergy Pump as Bridge-to-Transplant in Congestive Heart Failure, Thorac Cardiov Surg 2010; 58, Suppl. 2: S173-S178.

S. Klotz, B. Meyns, A. Simon, T. Wittwer, P. Rahmanian, C. Schlensak, T. Tdt Tjan, H.H. Scheld, D. Burkhoff—Partial Mechanical Long-Term Support with the CircuLite Synergy Pump as Bridge-to-Transplant in Congestive Heart Failure, Thorac Cardiov Surg 2010; 58, Suppl. 2: S173-S178, consisting of 6 pages.

\* cited by examiner

IMPLANTABLE MECHANICAL CIRCULATORY SUPPORT DEVICES

CROSS-REFERENCE TO RELATED APPLICATION

This application is related to and claims priority to U.S. Provisional Patent Application Ser. No. 62/270,156, filed Dec. 21, 2015, entitled IMPLANTABLE MECHANICAL CIRCULATORY SUPPORT DEVICES, the entirety of which is incorporated herein by reference.

STATEMENT REGARDING FEDERALLY SPONSORED RESEARCH OR DEVELOPMENT n/a

TECHNICAL FIELD

The present invention relates to mechanical circulatory support devices or "MCSDs." MCSDs are used to assist the pumping action of the heart. Certain MCSDs are used to assist the pumping action of a ventricle of the heart and, therefore, are referred to as "ventricular assist devices" or "VADs."

BACKGROUND

For example, as shown in U.S. Pat. Nos. 7,972,122; 8,007,254; and 8,419,609, the disclosures of which are hereby incorporated by reference herein and copies of which are attached hereto, one form of MCSD incorporates a generally cylindrical inner casing defining a flow path and a rotor mounted within the flow path for rotation about the axis of the flow path. The rotor is arranged to impel blood along the axis of the flow path. Electrical coils are mounted around the inner casing, and an outer casing surrounds the electrical coils. The coils provide a rotating magnetic field within the flow path. The rotor has a permanent magnetization that interacts with the rotating field so that the rotating field impels the rotor in rotation about the axis. The MCSD may include a volute that serves to redirect the flow from the axial direction to a direction transverse to the axis. The volute has an outlet connection that serves as the outlet connection of the MCSD.

Such a pump can be implanted within the thoracic cavity of a human patient as, for example, within the pericardial sack. The inlet end of the housing may be connected directly to the ventricle or connected to the ventricle by a short inlet cannula. The outlet connection may be connected, for example, to the aorta by an outlet cannula. Merely by way of example, a typical MCSD of this type has a capacity to pump about 7-10 liters per minute against a pressure difference or head of about 75 mm Hg, and thus can bear a substantial proportion or almost all of the pumping load typically carried by the left ventricle. Merely by way of example, the outer casing of such a pump may be about 21 mm in diameter, and the volute may have somewhat larger dimensions in a plane perpendicular to the axis.

Other MCSDs, such as those shown in U.S. Pat. Nos. 7,905,823 and 8,768,487 and in U.S. Patent Publication No. 2014/0275723, now U.S. Pat. No. 8,882,477, the disclosures of which are hereby also incorporated by reference herein include generally similar elements but are of smaller size. These MCSDs typically implanted outside of the thoracic cavity as, for example, under the skin within the soft tissues of the pectoral area. These devices typically are connected to the heart as, for example, to the left atrium by an inlet cannula extending from the location of the pump to the atrium. The outlet of the pump typically is connected to an artery as, for example, the subclavian artery. Because the pump is implanted outside of the thoracic cavity, remote from the heart, the implantation procedure is considerably less invasive. Typically, the cannula can be inserted into a chamber of the heart by a laparoscopic or catheter-based procedure and threaded through the tissues of the body to the location of the pump. The procedure for inserting the outlet cannula is also performed outside of the thoracic cavity. Moreover, because the pump is located outside of the thoracic cavity, the pump can be accessed readily if it becomes necessary to repair or replace it.

MCSDs intended for extra-thoracic placement typically have been configured to provide lower pumping capacity than MCSDs intended for intra-thoracic implantation. For example, a typical MCSD intended to extra-thoracic implantation may provide a blood flow of about 1-4 liters per minute at a 75 mm Hg head. These MCSDs thus carry a smaller proportion of the pumping load of the heart. Such pumps typically have smaller dimensions than pumps intended for intra-thoracic implantation.

Extra-thoracically implanted MCSDs typically are housed in a pocket within the soft tissues outside of the thoracic cavity. Such pockets normally are created by surgical procedures as, for example, separating skin or subcutaneous fat from the underlying muscular tissue or separating layers of muscular tissue from one another. In some instances, the tissues forming the wall of a pocket surrounding an extra-thoracic MCSD can erode. Such erosion arises from mechanical action of the MCSD against the surrounding tissues. Mechanical action of the MCSD can lead to inflammation and necrosis of the tissues surrounding the pocket, and can cause the pocket to become enlarged. This difficulty can be particularly pronounced where the pocket closely overlies bones such as ribs. Enlargement of the pocket may allow movement of the MCSD, which creates an uncomfortable sensation for the patient. In severe cases, these conditions may require correction by additional surgical procedures.

Certain aspects of the present invention provide MCSDs and implantation methods that can address these concerns. Moreover, the improved MCSDs and implantation methods may allow implantation of larger MCSDs in extra-thoracic locations. For example, MCSDs of the type typically used heretofore for intra-thoracic implantation can be implanted extra-thoracically.

SUMMARY

The present invention advantageously provides for a mechanical circulatory support device. The mechanical circulatory support device includes an inner casing defining a fluid flow path, the fluid flow path defines a longitudinal axis. A rotor is mounted within the fluid flow path and configured to rotate about the longitudinal axis. A housing is included, the inner casing and the rotor being substantially disposed within the housing. The housing having a cross-sectional shape in a plane transverse to the longitudinal axis which decreases in thickness extending from a medial position to opposite lateral positions.

In another aspect of this embodiment, the housing defines first surface disposed about the longitudinal axis and a second surface opposite the first surface, the first surface having a medial portion, the first surface being sloped on opposite sides of the medial portion toward the second surface.

In another aspect of this embodiment, the housing defines an opening to an interior of housing proximate the second surface.

In another aspect of this embodiment, the second surface is substantially planar.

In another aspect of this embodiment, the second surface is curved.

In another aspect of this embodiment, at least a portion of the second surface is sloped in a direction toward the longitudinal axis.

In another aspect of this embodiment, the medial portion is convex.

In another aspect of this embodiment, the first surface includes a pairs of end regions disposed on opposite ends of the first surface, and wherein the end regions are disposed substantially orthogonal to the longitudinal axis.

In another aspect of this embodiment, electrical coils are disposed within the inner cases and disposed about the longitudinal axis, the electrical coils being configured drive the rotor in rotation about the longitudinal axis.

In another aspect of this embodiment, an outer casing surrounding the electrical coils is included, the outer casing being substantially disposed within the housing, and wherein the outer casing is releasably attached to the housing.

In another aspect of this embodiment, electrical coils are configured to drive the rotor in rotation about the longitudinal axis, and wherein one or more electronic components are disposed within the housing, the one or more electronic components including power semiconductors connected to the electrical coils, the power semiconductors being configure to selectively conduct and selectively block current flow to the coils.

In another aspect of this embodiment, an outlet port extending through the housing is included, the outlet port being disposed transverse to the longitudinal axis and in communication with the flow path.

In another aspect of this embodiment, the rotor is an axial flow rotor configured to impel blood in a downstream direction along the flow path, and wherein the device further includes a volute disposed between the flow path and the outlet port.

In another embodiment, a method of implanting an MCSD includes forming a pocket within the body of the patient outside of the thoracic cavity. A housing is implanted within the pocket, the housing having an inner casing defining a fluid flow path and a longitudinal axis along the fluid flow path and a rotor mounted within the fluid flow path. The housing has a cross-sectional shape in a plane transverse to the longitudinal axis which decreases in thickness extending from a medial position to opposite lateral positions the medial position of the housing facing outwardly when the housing is implanted within the pocket. The fluid flow path is fluidly coupled to the circulatory system of the patient.

In another aspect of this embodiment, the pocket is formed in the pectoral region of the patient's body.

In another aspect of this embodiment, fluidly coupling the fluid flow path to the circulatory system includes connecting an inlet cannula between a ventricle of the heart of the patient and the housing and connecting an outlet cannula from the housing to an artery of the patient.

In another aspect of this embodiment, the rotor is an axial flow rotor configured to impel blood in a downstream direction along the flow path.

In another aspect of this embodiment, the housing includes an outlet port disposed transverse to the longitudinal axis and in communication with the flow path.

In another aspect of this embodiment, the housing is coupled to a volute, and wherein the volute is in fluid communication with the fluid flow path.

In yet another embodiment, the MCSD includes an inner casing defining a fluid flow path, the fluid flow path defining a longitudinal axis. An axial flow rotor mounted within the fluid flow path and configured to rotate about the longitudinal axis and to impel blood in a downstream direction along the flow path is included. A housing is included, the inner casing and the rotor being substantially disposed within the housing. The housing has a cross-sectional shape in a plane transverse to the longitudinal axis which decreases in thickness extending from a medial position to opposite lateral positions. The housing defines first surface disposed about the longitudinal axis and a second surface opposite the first surface. The first surface has a medial portion. The first surface is sloped on opposite sides of the medial portion toward the second surface and the second surface is substantially planar. An outlet port extends through the housing, the outlet port is disposed transverse to the longitudinal axis and in communication with the flow path. A volute disposed between the flow path and the outlet port is included.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

As used herein, relational terms, such as "first" and "second," "top" and "bottom," and the like, may be used solely to distinguish one entity or element from another entity or element without necessarily requiring or implying any physical or logical relationship or order between such entities or elements.

Figure 1:
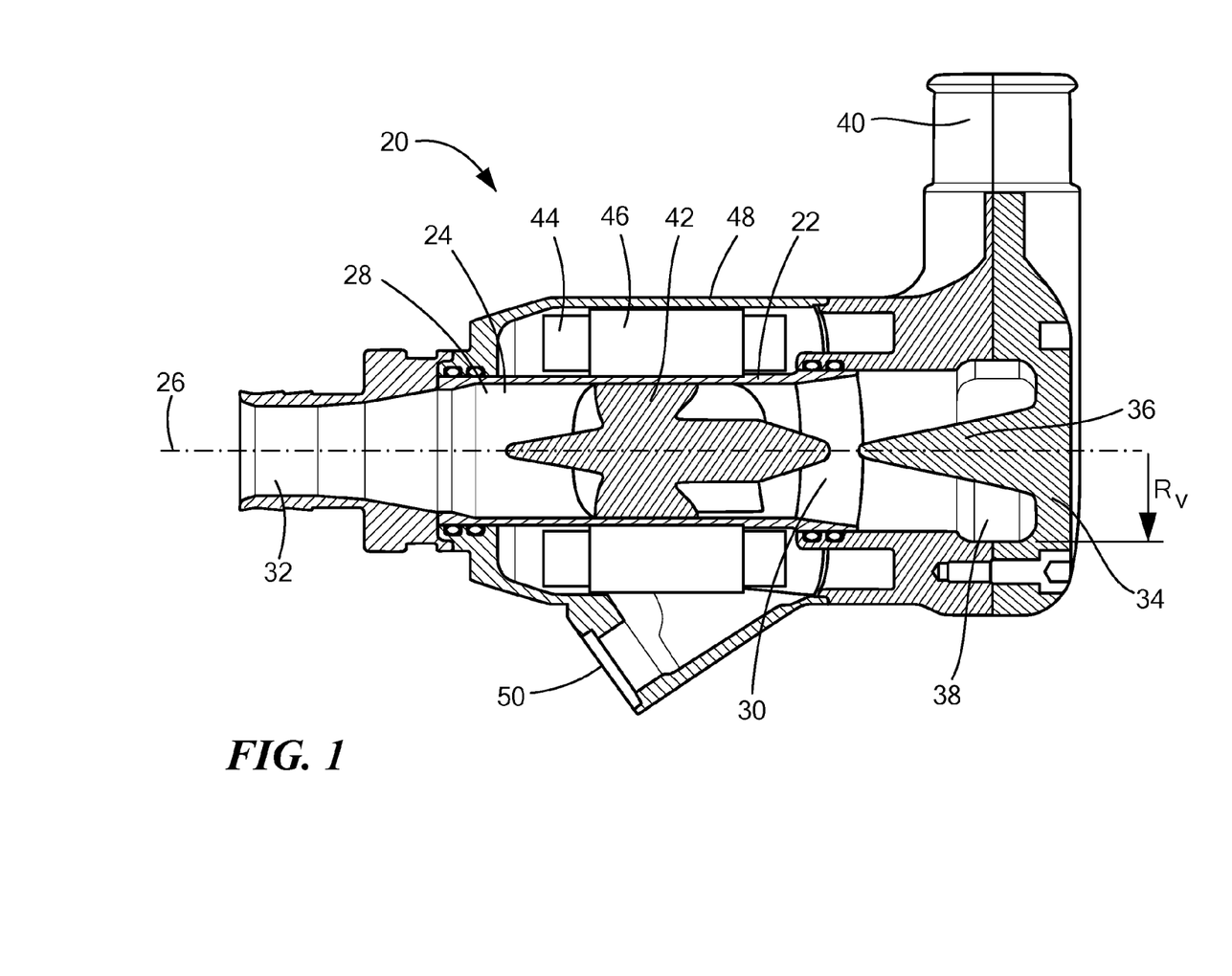
FIG. 1 is a diagrammatic sectional view depicting a pump used in one embodiment of the invention.
Figure 2:
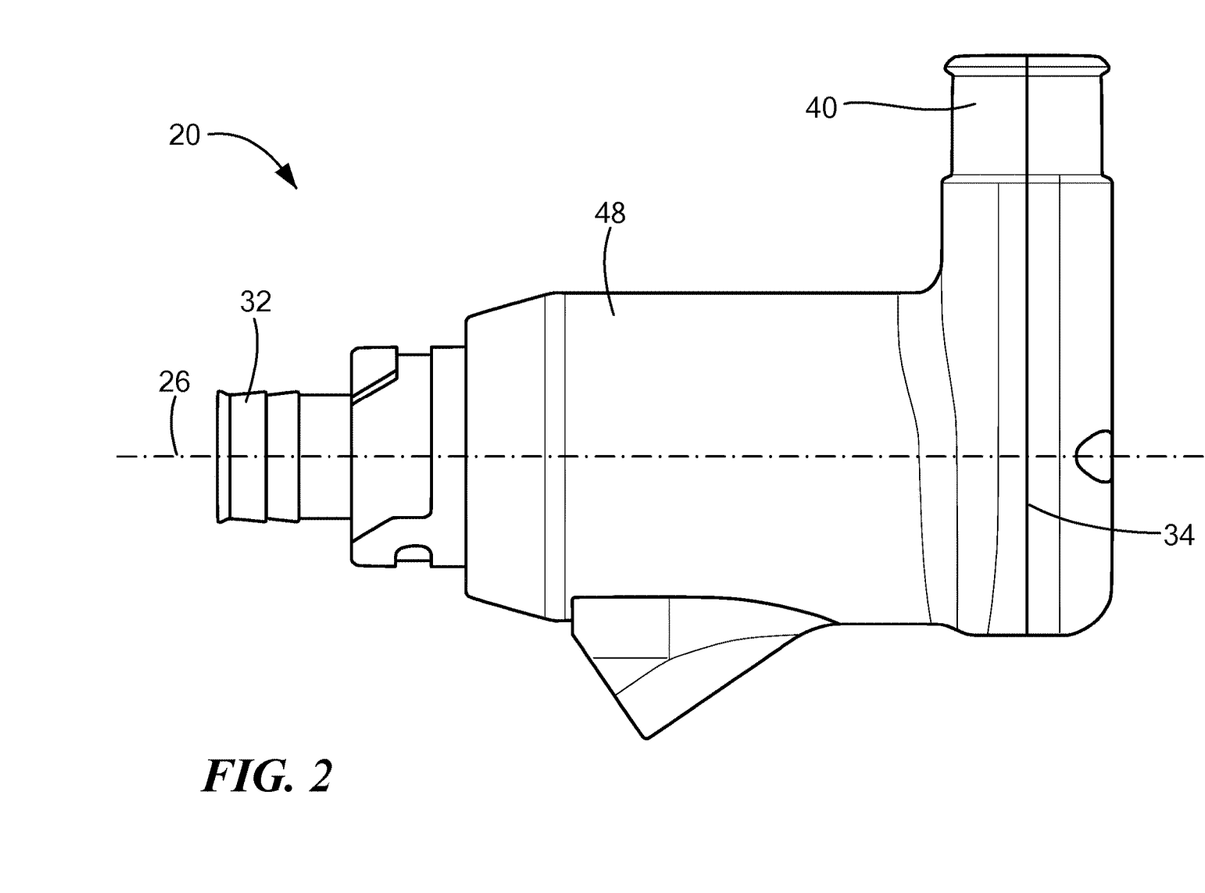
FIG. 2 is a plan view of the pump depicted in FIG. 2.

Now referring to the drawings in which like reference designators refer to like elements, there is shown in FIGS. 1-2 a blood pump for mechanical circulatory support device according to one embodiment of the invention and designated generally as "20". The blood pump 20 may be generally as disclosed in the aforementioned U.S. Pat. Nos. 7,972,122; 8,007,254; and 8,419,609. The blood pump 20 includes an inner housing 22 defining a generally cylindrical flow path 24 having an axis 26, an inlet end 28, and an outlet end 30. A hollow inlet fitting 32 projects axially from the inlet end 28 of the flow path 24 and is in fluid communication with the flow path 24. A volute 34 is provided at the outlet end 30 of the flow path. The volute 34 includes a center post 36 extending generally in the axial direction towards the flow path 24. The volute 34 defines a chamber 38 extending around the center post 36 and around axis 26. Chamber 38 has a radius $R_r$ measured from axis 26. The radius of the volute increases progressively in a circumferential direction around axis 26.

A tubular outlet port 40 extends in a plane transverse to axis 26 and is in fluid communication with the chamber 38 of the volute 34. In one configuration, the maximum radius Rv of the volute 34 is greater than the radius of the cylindrical flow passage 24. One particularly preferred form of volute is shown and described in the copending, commonly assigned U.S. provisional patent application No. 62/270,189, filed of even date herewith and entitled "AXIAL FLOW IMPLANTABLE MECHANICAL CIRCULATORY SUPPORT DEVICES WITH OUTLET VOLUTE," the disclosure of which is also incorporated by reference herein.

A rotor 42 is disposed inside the flow path 24 defined by inner casing 22. In one configuration, the rotor is symmetrical about an axis coincident with the central axis 26 of the flow path 24. In one configuration the rotor 42 includes plurality of vanes spaced circumferentially around the axis 26 and a plurality of channels between adjacent vanes. The vanes are configured to impel blood in the downstream direction along the axis upon rotation of the rotor about its axis in a predetermined direction. An exemplary rotor 42 is disclosed in U.S. Patent Application Publication No. 2015/0051438 ("the '438 Publication"), the disclosure of which is also incorporated by reference herein. As also explained in the U.S. Pat. Nos. 7,972,122; 8,007,254; and 8,419,609 and in the '438 Publication, the rotor 42 may be formed from a magnetic material such as a platinum-cobalt alloy and has a permanent magnetization in a direction transverse to the axis 26. The rotor 42 may further include hydrodynamic bearing surfaces on the tips of the vanes, remote from axis 26. The blood pump 20 further includes electrical windings 44 carried on ferromagnetic metal cores 46. The windings 44 typically are composed of numerous turns of wire encircling the cores. Windings 44 are disposed in an array around the outside of inner casing 22. As best appreciated with reference to FIG. 5, the windings are disposed in pairs, with the windings of each pair being diametrically opposed to one another on opposite sides of the axis 26.

As discussed further below, the windings 44 may be energized in alternating sequence using a three-phase excitation system so as to create a rotating magnetic field within the flow path 24. Magnetic coupling between this rotating field and the permanent magnetization of rotor 42 drives the rotor 42 in rotation about the axis 26 of the flow path. As described in the aforementioned patents, the hydrodynamic bearing surfaces on the rotor will maintain the rotor out of contact with the wall of inner casing 22 and with a thin film of blood disposed between the tip surface of each vane and the wall of the casing, and thus maintain the rotor with its axis aligned with the axis 26 of the flow path. Magnetic interaction between the magnetic field of the rotor and the ferromagnetic cores 46 of the stator prevents the rotor 22 from moving axially. Rotation of the rotor 42 drives blood in a downstream direction, from the inlet end 26 of the flow path to the outlet end 30 and out through the volute 34 and the outlet port 40.

An outer casing 48 surrounds the inner casing 22, the windings 44 and cores 46. In one configuration, the outer casing 48 is cylindrical and coaxial with the inner casing 22 and axis 26. The outer casing 48 forms a sealed enclosure around the windings 44. Electrical connections to the windings 44 may be made through an opening 50 in the outer casing 48, which may further be sealed.

Figure 3:
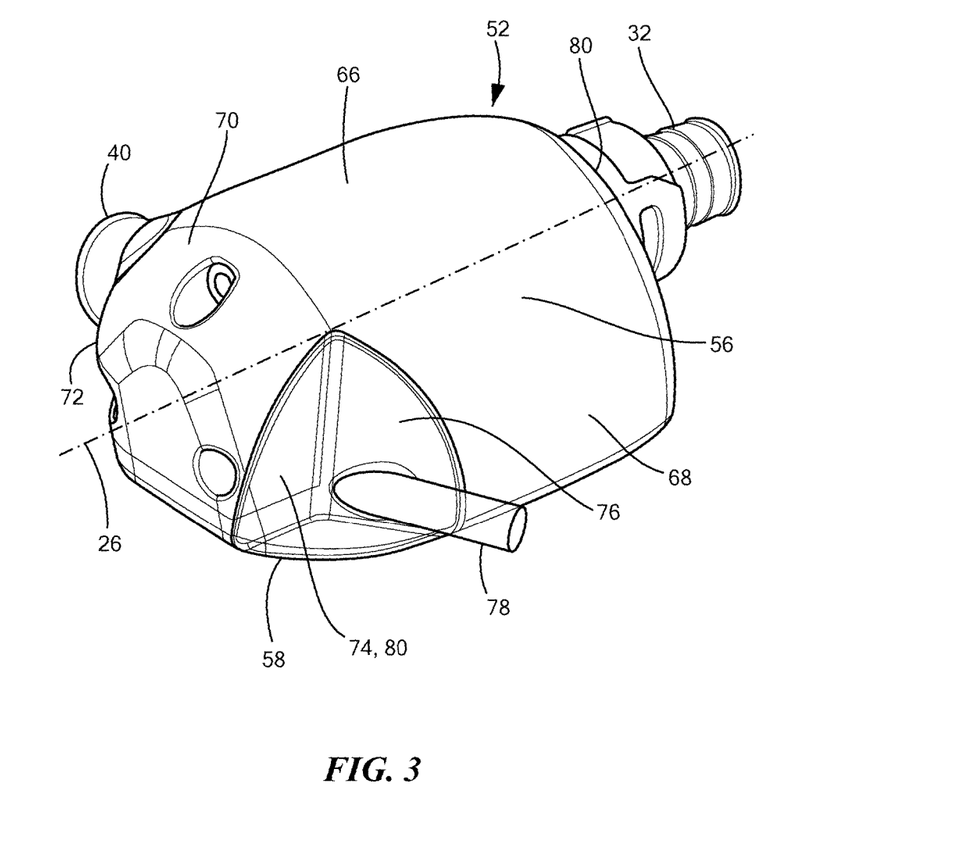
FIG. 3 is a perspective view of an MCSD incorporating the pump of FIGS. 1 and 2.
Figure 4:
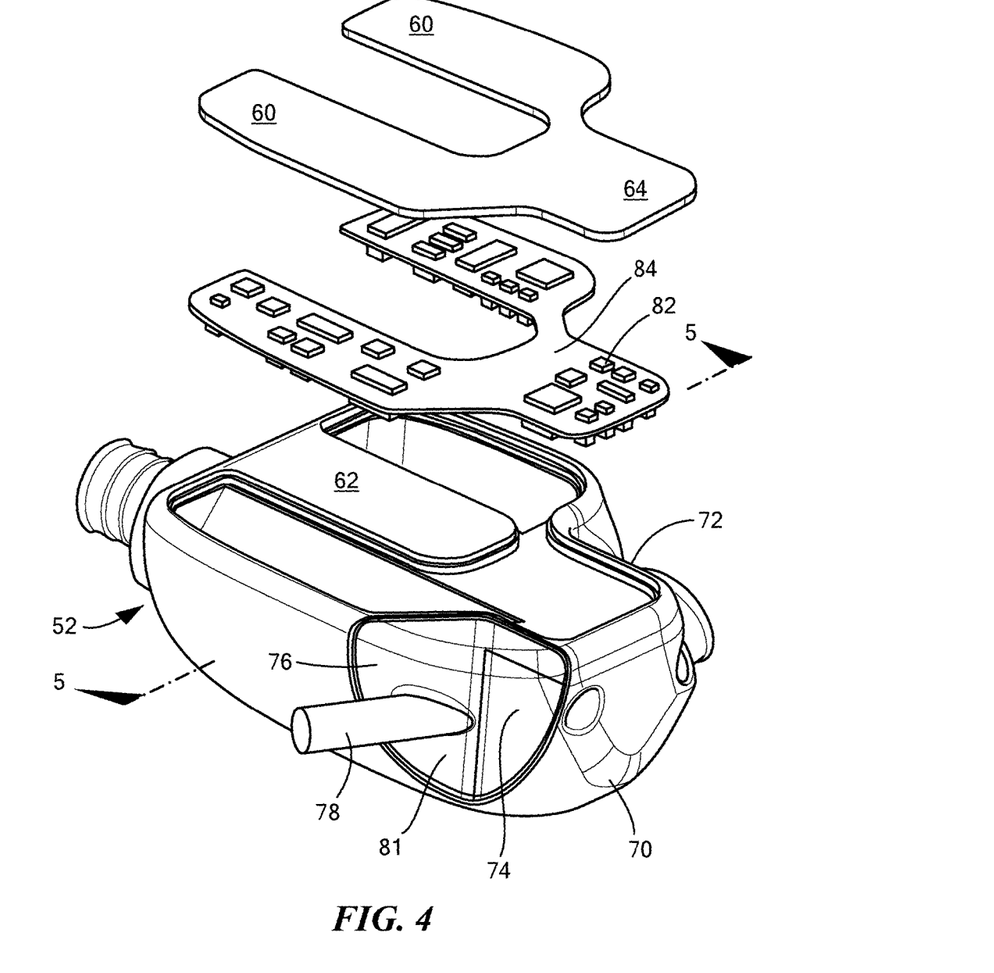
FIG. 4 is an exploded view of the MCSD shown in FIG. 3.
Figure 5:
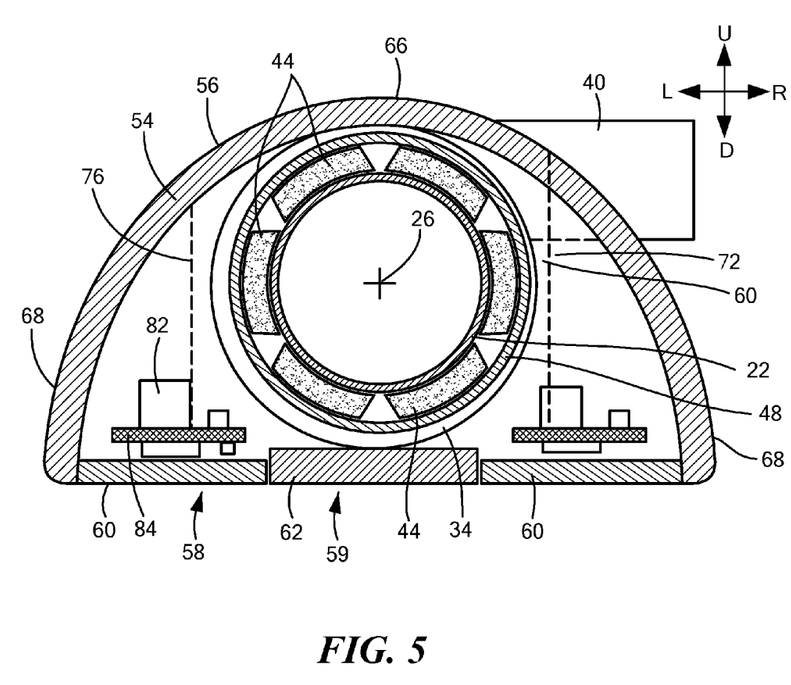
FIG. 5 is a diagrammatic sectional view taken along line 5-5 in FIG. 4.

Referring now to FIGS. 3-5, a housing 52 of the MCSD surrounds the outer casing 48 and the volute 34 such that the inner casing is at least substantially disposed within the housing 52. The housing 52 includes first surface 54 having a medial portion 56 defining a convex top surface 66 facing in an upward direction, transverse to the central axis 26 of the flow path 24 when the MCSD is implanted within the patient. The upward direction as used in this disclosure refers to a direction transverse to axis 26, indicated by arrow U in FIG. 5, whereas the downward direction as used in this disclosure refers to the opposite direction, indicated by arrow D. The upward direction is the direction that will face toward the outside or skin of the subject when the device is implanted. The housing 52 also includes a second surface or bottom wall 58 defining a downwardly facing bottom surface. In the particular embodiment depicted in FIGS. 4 and 5, bottom wall 58 includes a central element 62 and a pair of side elements 60. As best seen in FIG. 4, the side elements 60 are connected to one another by a tab 64 projecting generally in the axial direction from the side elements 60. In the embodiment of FIGS. 4 and 5, bottom surface 58 is a flat, downwardly facing surface. The medial portion 56 slopes downwardly, in lateral directions indicated by arrows L and R in FIG. 5, from the top surface 66 of the medial portion 56 disposed above the central axis 26 to edge regions 68 remote from the axis in the lateral direction. The first surface 54 slopes downwardly to a level below the axis 26. In one configuration, the medial portion 56 of housing 52 is aligned with the flow path 22 and outer casing 48, housing 52 has a cross-sectional shape that tapers gradually from a relatively large thickness adjacent the axis 26 to relatively small thicknesses at edge regions 68 remote from the axis 26 and offset from the axis 26 in opposite lateral directions transverse to the axis. In one configuration, the housing 52 is axially aligned with the inner casing 22, outer casing 48, and rotor 42, and the cross-sectional dimensions of the housing 52 are substantially uniform. Thus, the top portion 66 of the medial portion 56 lies at a constant elevation above the bottom surface 58, so that the housing 52 has substantially uniform thickness at the medial portion 56.

The housing 52 has an outlet end region 70 axially aligned with the volute 34 and with the outlet port 40. As best seen in FIGS. 4 and 5, the housing 52 has an indentation in the outlet end region 70 adjacent one edge region 68 so as to form a substantially vertical wall 72 extending upwardly from bottom wall 58 and intersecting the medial portion 56 between the top surface 66 of the medial portion 56 and edge region 68. A portion of the outlet port 40 of the volute 34 projects from within the housing 52 to outside of the housing 52. A portion of the outlet port 40 extends through the medial portion 56, whereas another portion of the outlet port 40 extends through the vertical wall 72. A further vertical wall 74 is also provided on the outlet end region 70 of the housing 52, on the side opposite from vertical wall 72. This vertical wall 72 also extends upwardly from the bottom wall 58 and faces in a lateral direction opposite to the lateral-facing direction of vertical wall 72. A further vertical wall 76 faces generally axially so that walls 74 and 76 cooperatively define a notch in the housing 52. An electrical cable 78 extends into the housing 52 through this notch and through wall 76. A shroud 81, shown in FIG. 4 as transparent, covers the cut-away portion. The shroud 81 defines a smooth surface continuous with the first surface 54 of the housing 52. The top surface 66 of the medial portion 56 curves downwardly within outlet end portion 70 in an axial direction toward the end of the housing 52, so that the housing 52 has a rounded profile if seen in an elevational view transverse to the axis. The housing 52 has an inlet end portion 80 adjacent the inlet fitting 32. Here again, the medial portion 56 curves downwardly within the inlet end portion 80. Within the inlet end portion 80 and within the outlet end portion 70, the bottom edge of the housing 52 curves inwardly toward the axis 26, so that the bottom surface 58 of the housing has rounded edges.

Electrical components 82 are mounted within the housing 52. As best seen in FIGS. 4 and 5, the electrical components 82 are disposed on a circuit board 84 and are disposed adjacent the edges regions 68 of the housing 52. Stated another way, some or all of the electrical components 82 lie adjacent the edge regions 68 of the housing 52, laterally remote from the axis 26. Within these edge regions 68, the housing 52 provides space above the circuit board 84 so that components 82 of substantial size can be mounted. The electrical components 82 are directly or indirectly connected to the coils 46 of the pump 20. For example, the electrical components 82 may include switching elements such as field effect transistors that are used to make and break electrical connections between the various coils and power and ground voltages, so as to produce the rotating magnetic field to drive the rotor. In a typical circuit of this type, a pump with three pairs of opposed coils may require six separate switching elements and six connections between switching elements and coils. These connections carry the full power used to drive the coils. Where the switching elements are disposed inside the housing 52, these connections need extend only within the housing 52. Thus, in one configuration, only two power leads—a ground connection and a supply voltage connection—extend out of the housing, along with any desired control signal leads. By contrast, where the switching elements are disposed in a controller separate from an MCSD housing 52 containing the pump 20, six power leads extend to the MCSD. Reducing the number of power leads allows the use of a substantially smaller cable for feeding power to the MCSD and thus simplifies installation of the cable. Alternatively or additionally, other electrical components 82 may be disposed within the housing 52. For example, the other electrical components 82 may be used to perform some or all of the functions of a pump controller. Typically, the pump controller monitors operation of the pump, actuates the switching elements to provide the desired rotor speed and flow characteristics. The controller may also performs additional functions such as providing alarm signals denoting abnormal conditions, recording abnormal events during operation and the like. Pump controllers are known in the art; certain controllers are described, for example, in U.S. Pat. Nos. 8,628,460 and 8,597,350, the disclosures of which are hereby incorporated by reference herein. Some or all of the components 82 that perform the controller functions may be disposed within the housing. Even where the switching elements are disposed external to the housing 52, some or all of the controller components may be mounted within the housing 52. Mounting some of the controller components within the housing 52 reduces the bulk of a separate controller housing. Where all of the controller components are mounted within the housing of the MCSD itself, there is no need for a separate controller housing.

Figure 6:
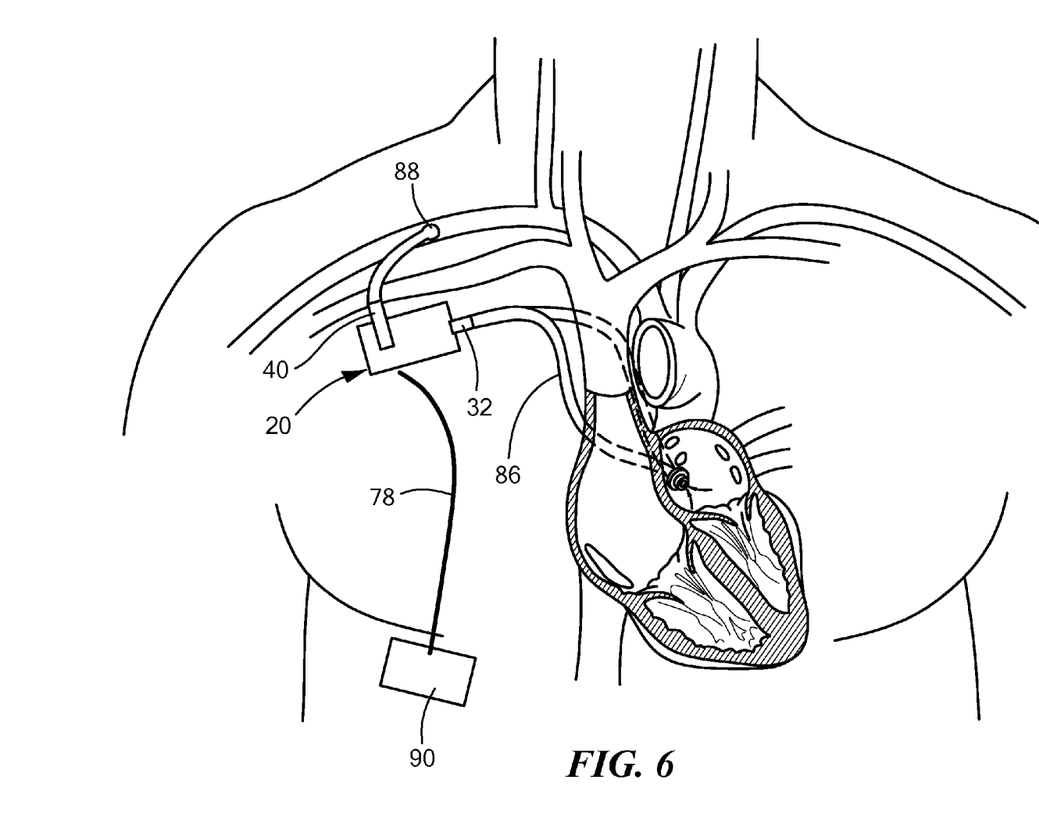
FIG. 6 is a diagrammatic view depicting the MCSD of FIGS. 3-5 implanted in a human patient.

In a method according to a further aspect of the invention, the MCSD discussed above is implanted within the body of a human or non-human mammalian patient, at a location outside of the thoracic cavity of the patient as depicted in FIG. 6. The implantation procedure includes forming a pocket within the body of the patient at the location where the MCSD is to be implanted. Typically, the pocket is formed by forming a cut in tissues of the subject and separating adjacent layers of tissue. The MCSD is then inserted between the separated layers. In one configuration, the pump 20 is positioned in the pocket with the top surface 66 of the housing 52 facing upwardly, toward the skin of the subject, and with the bottom surface 58 facing downwardly, toward the interior of the patient's body. Before or after insertion into the pocket, the inlet fitting 32 (FIG. 3) is connected to a source of blood by a flexible elongated inlet cannula 86. The outlet port 40 is connected to an artery by an outlet cannula 88. Most typically, where the MCSD is used to assist the pumping action of the left side of the heart, supporting the general circulation, the inlet cannula 86 is connected to the left atrium or left ventricle of the heart, and the outlet cannula 88 is connected to an artery of the general circulation as, for example, the subclavian artery.

The drive line 78 is connected to a source of power and control signals 90. Such a source may be an implanted controller or a connection such as a skin-penetrating connection to an external controller worn by the subject. In other embodiments, the source 90 of power and control signals may incorporate a transcutaneous energy transfer or "TET" arrangement for transferring electrical energy through the skin without a physical skin-penetrating connection. For example, a TET may incorporate an induction coil disposed within the patients's body and another induction coil disposed outside of the patient's body. The procedures used for installing the inlet cannula 86, outlet cannula 88, and drive line 78 may be substantially conventional. For example, each of these elements may be "tunneled" through the patient's body. Where an implanted controller is used, power may be supplied to the controller through a skin-penetrating connection or through a TET arrangement. A battery (not shown) may be included in the controller or may be disposed in a separate implanted battery housing (not shown) so as to provide temporary power when external power is disconnected.

Figure 7:
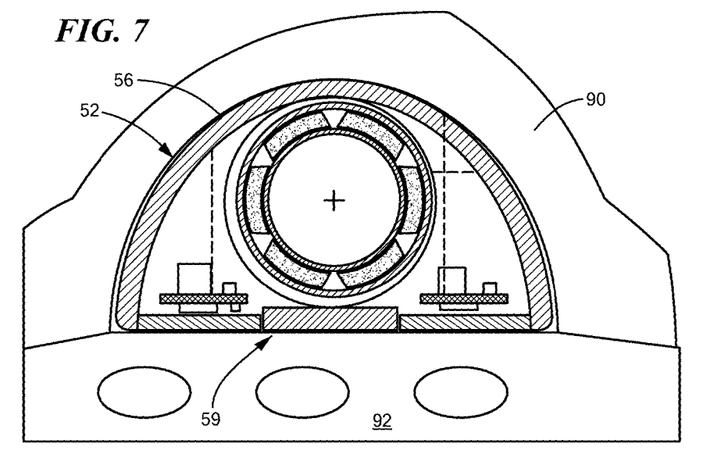
FIG. 7 is the MCSD shown in FIG. 5 in an implanted condition.

As schematically illustrated in FIG. 7, the housing 52 provides a shape that allows conformance of the tissue layers with the housing 52, and which tends to minimize severe stresses on the tissues surrounding the pocket. The medial portion 56 allows the overlying tissues 90 to conform to the housing 52 so that the tissue contacts the housing 52 over a relatively large area and thus distributes stresses on the tissue caused by implantation of the MCSD. Likewise, the bottom surface 58 spreads the load over the underlying tissue layer 92.

Figure 8:
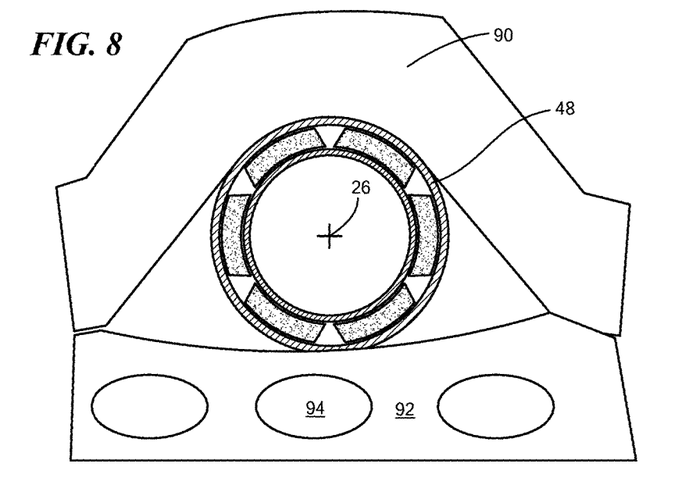
FIG. 8 is a view similar to FIG. 7 depicting the pump of FIGS. 1 and 2 implanted in the patient.

Now referring to FIG. 8, by contrast, an MCSD incorporating a generally similar pump 20 without housing 52 is shown in an implanted condition in FIG. 8. The outer casing 48 tends to engage the tissue only in areas close to the axis 26. This implies relatively high concentrated loads applied between the casing and the tissue layers 90 and 92. Such concentrated loads tend to promote necrosis of the tissue. Moreover, the overlying tissue layer 90 is in tension, which may tend to promote peeling or separation of the tissue layers around the pocket at the junctures of the tissue layers. The concentrated loads are particularly problematic where one of the tissue layers includes boney structures. For example, if the pump 20 without the housing is implanted as shown in FIG. 8 over a layer that includes boney structures 94 and if the pump 20 outer casing 48 is disposed close to one of these boney structures 94, the tissue between the outer casing 48 and the boney structure 94 can be compressed to such a degree that blood circulation to the tissue is impaired. By contrast, in an MCSD having the housing 52 discussed above with reference to FIGS. 3-5, the relatively wide distribution of force over the bottom surface 58 of the housing 52 (FIG. 7) tends to avoid this problem.

Figure 9:
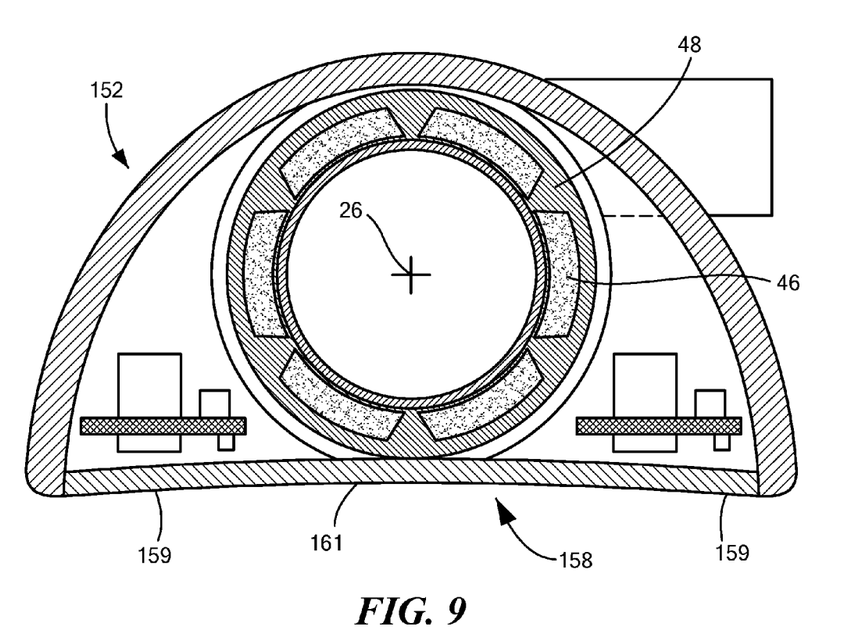
FIG. 9 is diagrammatic sectional view depicting an MCSD according to another embodiments of the invention.

The embodiments discussed above can be varied in numerous ways. For example, as shown in FIG. 9, the outer casing of the pump is omitted. In this arrangement, the stator, including the core 46 and coils 44, is exposed to the environment within housing 152 so that the coils and their electrical connections are protected from the environment within the subject's body only by the housing. This permits some reduction in the thickness of the housing at its medial portion adjacent the axis. Also, in this arrangement, the bottom wall 158 is concave, so that the bottom surface slopes upwardly in the lateral directions from edge regions 159 remote from the axis 26 of the pump to a medial region adjacent the axis. This concavity can be useful where the MCSD is installed in a pocket within a naturally convex region of the subject's body. In other respects, the embodiment of FIG. 9 is generally similar to the embodiments discussed above.

Figure 10:
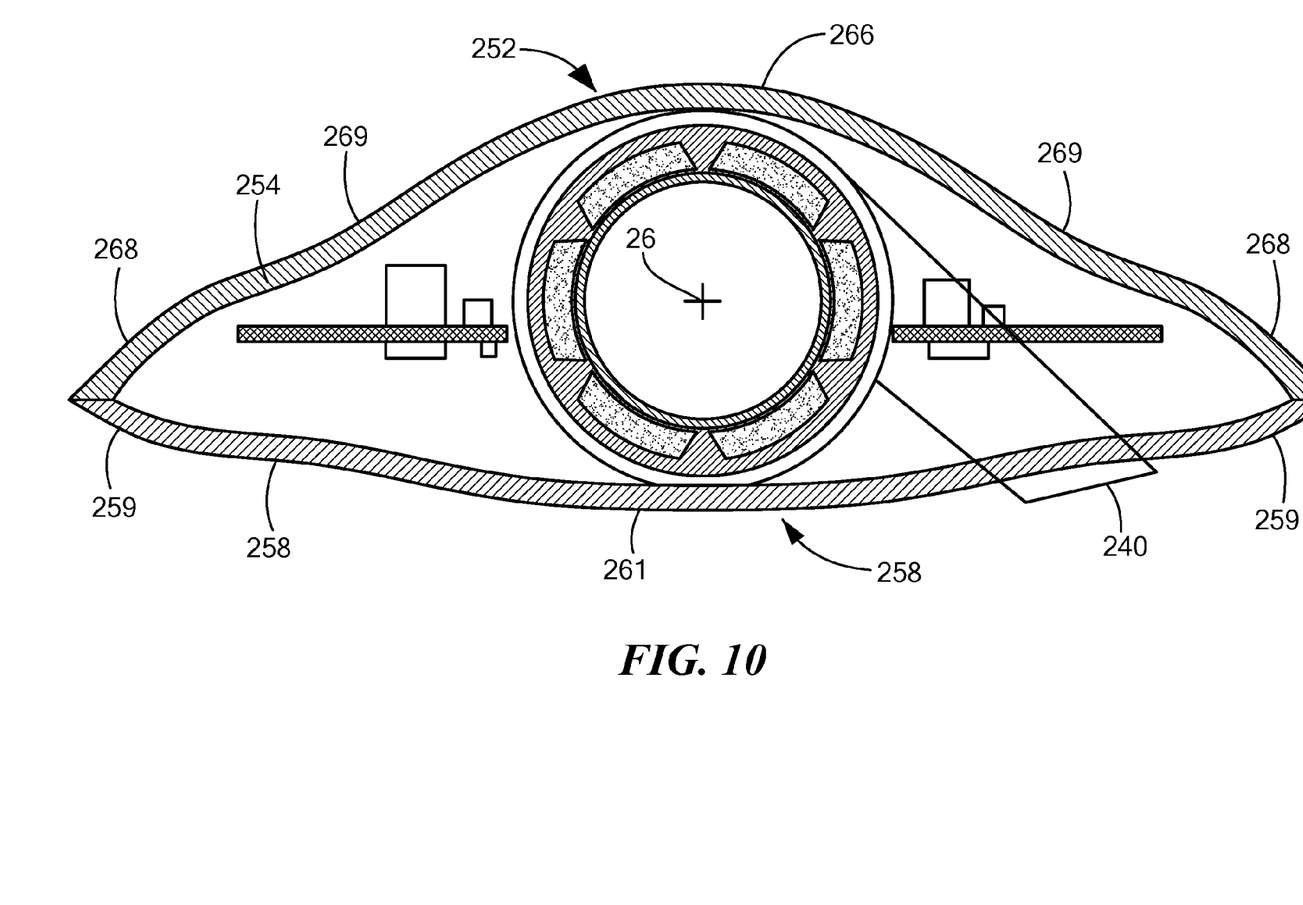
FIG. 10 is diagrammatic sectional view depicting an MCSD according to another embodiments of the invention.

In the embodiment of FIG. 10, the bottom surface 258 is generally convex, rather than concave, so that the bottom surface slopes downwardly from edge regions 259 laterally remote from the axis of the pump to medial regions 261 adjacent the axis. Also in this embodiment, the top surface 252 is generally convex and provides a smooth, downwardly sloping surface extending from the medial region adjacent the axis to edge regions 268 laterally remote from axis 26. In this embodiment, although the top surface 252 is generally convex, it includes some local regions 269 where it is slightly concave. Stated another way, a generally convex surface need not be entirely convex at every point. In the embodiment of FIG. 10, the convexity of the bottom surface 258 is less than the convexity of the top surface. Stated another way, the top wall 254 has a greater vertical extent (in the upward and downward directions) than the bottom wall 258. The top and bottom walls meet at junctures defined by edge regions 259 and 266. These junctures are disposed below the axis 26 of the pump components. In the embodiment of FIG. 10, the outlet port 40 is directed downwardly as well as laterally and exits through the bottom surface 258 of the housing.

Figure 11:
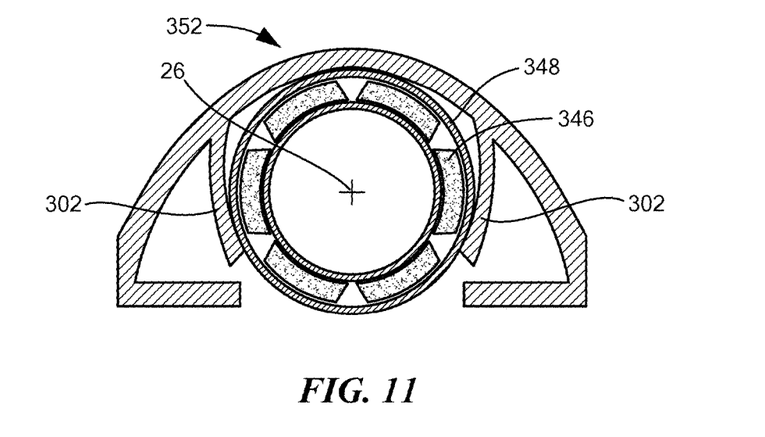
FIG. 11 is diagrammatic sectional view depicting an MCSD according to another embodiments of the invention.
Figure 12:
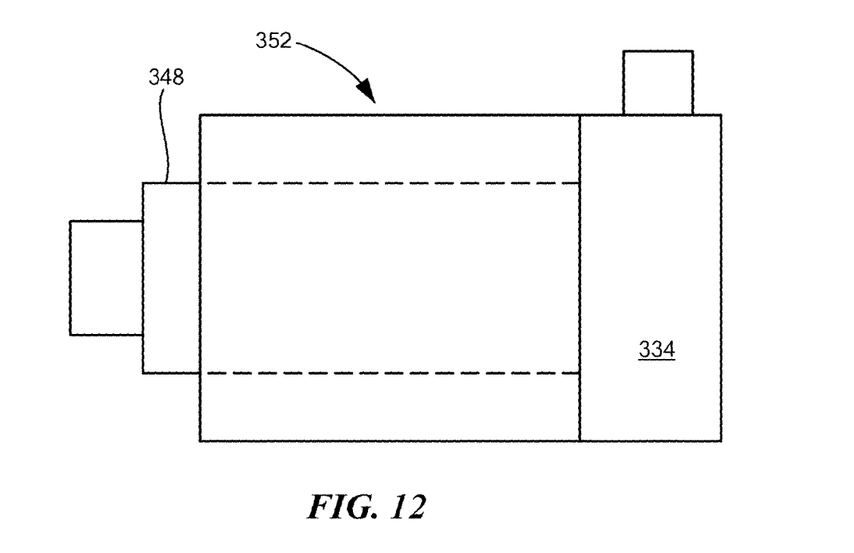
FIG. 12 is a diagrammatic plan view of the MCSD of FIG. 11.

The embodiment of FIG. 11 includes a pump having an external casing 348 surrounding the windings 346. Thus, in this case, the windings and other electrical components of the pump are protected by the external casing. The housing 352 is not sealed. The housing includes resilient elements 302 adapted to releasably engage the outer casing of the pump. Also, in this embodiment, the bottom surface 358 has an opening in the medial region, adjacent the axis 26 of the pump. In this embodiment as well, housing 352 has a cross-sectional shape, when viewed in a direction parallel to the axis of the pump, which tapers from a relatively large thickness at medial regions close to the axis to a relatively small thickness laterally remote from the axis. As best seen in FIG. 12, a top view of the assembled pump and housing, housing 352 encompasses only a portion of outer casing 348. The volute 334 projects axially beyond housing 352 at one end of the housing, whereas casing 348 of the pump projects axially beyond housing 352 at the opposite end. A housing of this nature can be readily installed on a pump that was originally manufactured without the housing 352, simply by forcing the pump casing into the housing until it is engaged between resilient elements 302. In this arrangement, the electronic elements associated with the pump are either housed within the casing 348 of the pump itself or within a separate controller housing. In a variant of this approach, the bottom surface 358 may be continuous across the entire lateral extent of the housing so that opening 304 is omitted. In this arrangement, the casing of the pump may be inserted into the housing by moving it into the housing axially. In a further variant, the wall defining the bottom surface of the housing may be movable between a closed position, in which it extends laterally across the bottom of the housing, and an open position.

Figure 13:
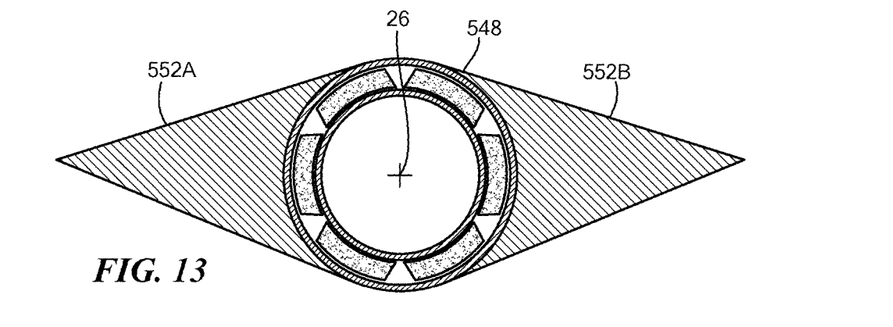
FIG. 13 is diagrammatic sectional view depicting an MCSD according to another embodiments of the invention.

In the embodiment of FIG. 13, the housing includes two separate housing elements 552a and 552b, which are attached to laterally opposite sides of the pump casing 548. Portions of the pump housing 548 are exposed at medial regions of the combined structure. The combined shape defined by the pump housing 548 and by housing elements 552a and 552b again includes a relatively large thickness dimension (in the upward and downward directions) at locations laterally adjacent axis 26 and again tapers to a relatively small dimension at edges remote from the axis in opposite lateral directions. The housing still serves to distribute the loads applied between the tissue layers and the MCSD.

Figure 14:
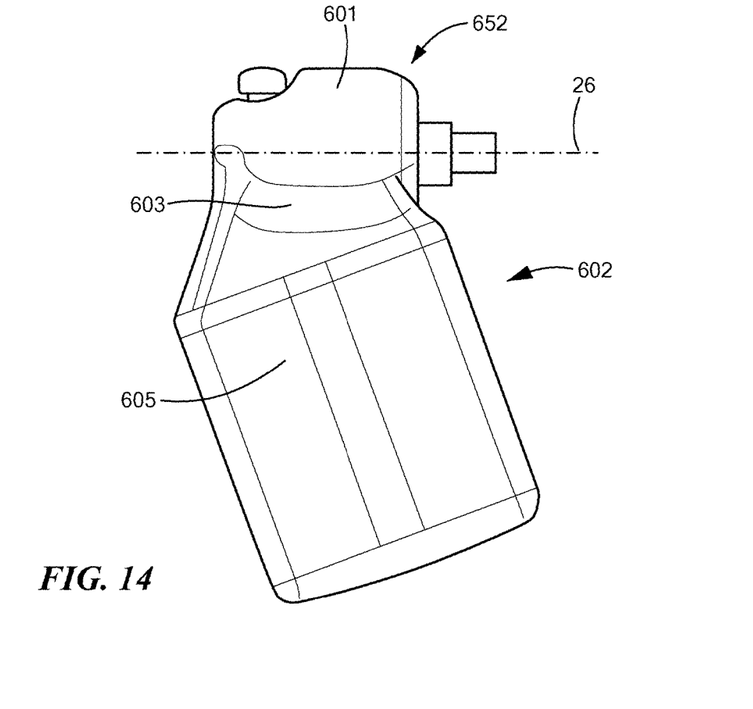
FIG. 14 is diagrammatic sectional view depicting an MCSD according to another embodiments of the invention.

An MCSD according to yet another embodiment of the invention (FIG. 14) includes a housing 652 which includes a main section 601 housing the pump. Main section 601 may be generally similar to any of the housings discussed above. The housing 652 further includes an additional section 602 extending laterally from the main section 601. Section 602 includes a portion 603 containing electronics and a further portion 604 containing a battery. Preferably, the only implantable battery used to power the pump is disposed in housing 652, and the implantable controller is entirely contained within the housing. This arrangement provides a simpler implantation procedure, as well as reduced electrical losses because there is no need for long cables connecting implanted components to one another. Typically, a driveline is connected between housing 652 and a component such as a percutaneous connector used to supply power and signal connections to outside of the body. In a further variant, the internal coil of a transcutaneous energy transfer system and telemetry devices may be disposed within the housing, so that only the housing and cannulas need be implanted. In yet another variant, the internal coil of a TET coil may be mounted in any of the housings discussed above. The features of the various embodiments discussed above can be combined with one another. For example, the separate housing elements shown in FIG. 13 can be hollow and can house components such as electrical components.

In another variant, where the housing 352 is open to the environment within the subject as, for example, in the embodiment of FIGS. 11 and 12, the bottom wall may be entirely omitted. Also, in an embodiment where the bottom wall 358 is entirely omitted, or where the bottom wall has an opening, the pump casing may project slightly below the remainder of the housing.

The housings may be formed of various materials. Where the housing is intended to provide a sealed arrangement, the housing should have relatively low permeability to moisture. The housing may be formed of a metal or from a composite including a metal or other impervious material. The housing may be rigid or flexible and may have varying degrees of rigidity or flexibility. Also, the exterior surfaces of the housing, such as the top and bottom surfaces discussed above, may be provided with a porous material or other material that promotes ingrowth of tissue so as to securely bond the MCSD in place within the pocket.

In the embodiments above, the pump has been described as an axial flow pump. However, the present invention also can be applied to radial flow pumps. A radial flow pump likewise has a rotor rotatable about an axis within a flow path. In a radial flow pump, however, the fluid flow within the rotor is primarily in the radial direction, away from the axis. Likewise, the present invention can be applied in connection with mixed-flow pumps, in which the fluid flow within the rotor has substantial axial and radial components.

As these and other variations and combinations of the features described above can be employed, the foregoing description should be taken by way of illustration rather than by limitation of the present invention. Additional features of the present invention are disclosed in the numbered paragraphs set forth below:

What is claimed is:

1. An mechanical circulatory support device, comprising:
   an inner casing defining a fluid flow path, the fluid flow path defining a longitudinal axis;
   a rotor mounted within the fluid flow path and configured to rotate about the longitudinal axis and pump fluid along the longitudinal axis; and
   a housing, the inner casing and the rotor being substantially disposed within the housing, the housing having a cross-sectional shape in a plane transverse to the longitudinal axis, the housing defines a first surface disposed about the longitudinal axis and a second planar surface transverse the longitudinal axis.

2. The device of claim 1, wherein the housing defines an opening to an interior of housing proximate the second surface.

3. The device of claim 1, wherein the second surface is substantially planar.

4. The device of claim 1, wherein the second surface is curved.

5. The device of claim 1, wherein at least a portion of the second surface is sloped in a direction toward the longitudinal axis.

6. The device of claim 1, wherein the medial portion is convex.

7. The device of claim 6, wherein the first surface includes a pairs of end regions disposed on opposite ends of the first surface, and wherein the end regions are disposed substantially orthogonal to the longitudinal axis.

8. The device of claim 1, further including electrical coils disposed within the inner cases and disposed about the longitudinal axis, the electrical coils being configured drive the rotor in rotation about the longitudinal axis.

9. The device of claim 8, further including an outer casing surrounding the electrical coils, the outer casing being substantially disposed within the housing, and wherein the outer casing is releasably attached to the housing.

10. The device of claim 1, further including electrical coils configured to drive the rotor in rotation about the longitudinal axis, and wherein one or more electronic components are disposed within the housing, the one or more electronic components including power semiconductors connected to the electrical coils, the power semiconductors being configure to selectively conduct and selectively block current flow to the coils.

11. The device of claim 1, further including an outlet port extending through the housing, the outlet port being disposed transverse to the longitudinal axis and in communication with the flow path.

12. The device of claim 11, wherein the device further includes a volute disposed between the flow path and the outlet port.

13. An mechanical circulatory support device, comprising:
   an inner casing defining a fluid flow path, the fluid flow path defining a longitudinal axis;
   an axial flow rotor mounted within the fluid flow path and configured to rotate about the longitudinal axis and to impel blood in a downstream direction along the flow path;
   a housing, the inner casing and the rotor being substantially disposed within the housing, the housing having a cross-sectional shape in a plane transverse to the longitudinal axis, the housing defines a first surface disposed about the longitudinal axis and a second planar surface transverse the longitudinal axis, the housing having a convex shape;
   an outlet port extending through the housing, the outlet port being disposed transverse to the longitudinal axis and in communication with the flow path; and
   a volute disposed between the flow path and the outlet port.

* * * * *